United States Patent [19]
Dubois

[11] Patent Number: 4,962,253
[45] Date of Patent: Oct. 9, 1990

[54] VINYLATION OF AROMATICS CATALYZED BY CYCLOPENTADIENYL, INDENYL, OR FLUORENYL RHODIUM COMPLEXES, AND NOVEL INDENYL AND FLUORENYL RHODIUM COMPLEXES

[75] Inventor: Robert A. Dubois, Houston, Tex.

[73] Assignee: The Dow Chemical Company, Midland, Mich.

[21] Appl. No.: 397,150

[22] Filed: Aug. 21, 1989

[51] Int. Cl.$^5$ .......................... C07C 15/46; C07C 2/64
[52] U.S. Cl. .................................... 585/438; 585/457; 556/136
[58] Field of Search ................. 585/438, 457; 556/136

[56] References Cited

U.S. PATENT DOCUMENTS

| | | |
|---|---|---|
| 2,818,416 | 12/1957 | Brown et al. |
| 3,159,659 | 12/1964 | Pruett et al. |
| 3,636,122 | 1/1972 | Cramer et al. ....................... 556/136 |
| 3,883,634 | 9/1974 | Pruett et al. |
| 4,111,975 | 9/1978 | Cawse et al. ......................... 502/161 |
| 4,118,339 | 10/1978 | Latos ..................................... 502/27 |
| 4,263,212 | 4/1981 | Hong et al. .......................... 585/438 |
| 4,293,724 | 10/1981 | Beach et al. .......................... 585/457 |
| 4,717,783 | 1/1988 | Dubois et al. |
| 4,751,344 | 6/1988 | Walker ................................. 585/656 |

OTHER PUBLICATIONS

Shimizu "Shrene from Benzene and Ethylene" 1978 Chem. Absts. vol. 89, #90442.
Cramer et al., *Nucleophilic Displacement of Ethylene From* $\pi C_5H_5Rh(C_2H_4)_2$, J. Organometallic Chem., 92(1975) 245–252.
Caddy et al., *Reactivity of η5-indenylrhyodium(I)Complexes; Cyclocotrimerization of Alkynes with Alkenes,* Angew. Che. Int. Ed. Engl. 16(1977) No. 9, 648–649.
Marder et al., *The Slip-Fold Distortion of π-Bound Indenyl Ligands. Dynamic NMR and X-ray Crystallographic Studies of (η-indenyl)RhL$_2$ Complexes,* Organometallics 1987, 6, 2012–2014.
Hong et al., *Rhodium Carbonyl-Catalyed Activation of Carbon-Hydrogen Bonds for Application Organic Synthesis. V. Phenylation of Olefins with Benzenes,* J. Molecular Catalysis, 26(1984) 297–311.
Mildyrin, *C–H vs. O–H Reductive Elimination of Methanol from a Metal Complex. Which is a More Likely Process?,* J. Am Chem. Soc. 1986, 108, 3525–3526.
Hong et al., *Reactions of Ethylene and Benzenes Catalyzed by Rhodium Carbonyls Under Carbon Monoxide. The Formation of Styrenes and 3-Pentanone,* Chem. Soc. of Japan, Chem. Letters, pp. 1335–1336, 1979.
Rerek et al., *Kinetics and Mechanism of Substitution Reactions of* η5-*Cyclopentadienyldicarbonylrhodium(I)Derivatives. Rate Enhancement of Associative Substitution in Cyclopentadienylmetal Compounds,* J. Am. Chem. Soc. 1984, 106, 5908–5912.
Caddy et al., *Evidence for the Ready Insertion of Rhodium into a Carbon-Hydrogen Bond of Ethylene; Crystal and Molecular Structure of* μ-*Bet-2-ene-*μ-*ethylene-bus-(η5-1-methylindenyl)dirhodium,* J.C.S. Chem. Comm., 1978, 839–841.
Mlekuz et al., *X-ray Crystal Structure and Molecular Dynamics of (Indenyl)bis(ethylene)rhodium(I): 500-MHz NMR Spectra and EHMO Calculations,* Organometallics 1986, 5, 1656–1663.
Borrini et al., *Highly Active Rhcodium Catalysts for the [2+2+2]Cycloaddition of Acetylenes,* J. Molecular Catalysis, 30(1985) 181–195.
Seiwell, *Hydrogen-Deuterium Exchange between* η5-$C_5H_5Rh(C_2H_4)_2$ *and Aromatic Hydrocarbons,* J. Amer. Chem. Soc., 1974, 7134–7135.
Seiwell, *Protonation of Rhodium-Olefin Complexes,* Inorganic Che., vol. 15, No. 10, 2560–2563, 1976.
*Kirk-Othmer Encyclopedia of Chemical Technology,* 3rd Ed., vol. 21, 770–786.
Caddy et al., *Reactions of Co-ordinated Ligands. Part 22.1 The Reactivity of Bis-(ethylene(η5-indenyl)rhodium in Displacement Reactions with Olefins, Dienes, and Acetylenes; Crystal Structure of* η5-*indenyl[1-2:3-4-*η4-*[6-endo-propen-2-yl-1,2,3,4-tetrakis(trifluoromethyl)cyclohexa-1,3-diene]}rhodium formed in a Cyclo-cotrimerisation Reaction,* Chem. SOc., London, J. C. S. Dalton, 962–972 (1980).
King et al., *Organometallic Chemistry of the Transition Metals. III. Reactions between Sodium Cyclopentadienide and Certain Complex Transition Metal Halides,* Organometallic Chem. of transition Metals, vol. 2, No. 3, Jun., 1963, 528–531.

*Primary Examiner*—Helen M. S. Sneed
*Assistant Examiner*—J. Saba
*Attorney, Agent, or Firm*—Ann K. Galbraith

[57] ABSTRACT

A process for the preparation of vinyl aromatic compounds comprises contacting an aromatic compound and an olefin in the presence of a catalytic amount of a cyclopentadienyl, indenyl, or fluorenyl rhodium complex under reaction conditions sufficient to form the corresponding vinyl aromatic compound. Novel alkyl- or trimethylsilyl-substituted indenyl or fluorenyl compounds are among the compounds suitable for use in the process of the invention.

13 Claims, No Drawings

VINYLATION OF AROMATICS CATALYZED BY CYCLOPENTADIENYL, INDENYL, OR FLUORENYL RHODIUM COMPLEXES, AND NOVEL INDENYL AND FLUORENYL RHODIUM COMPLEXES

BACKGROUND OF THE INVENTION

This invention relates to catalytic processes for preparing vinyl aromatic compounds and to metal complexes used as catalysts in such processes.

Many processes for making vinyl aromatic compounds are known. Most, however, require two or more chemical steps from the aromatic starting material. For example, styrene may be produced in two steps by the alkylation of benzene to ethylbenzene, and the dehydrogenation of ethylbenzene to styrene. See, for example, Lewis, P. J.; Hagopian, C.: Koch, P.: Kirk-Othmer Encyclopedia of Chemical Technology, Third Ed., Vol. 21, p. 770, John Wiley & Sons (1983).

Several processes are known which require only one step from the olefin and aromatic compound to the corresponding styrenics. Kozhevnikov, 1. V. and Matveev, K. I., "On the Mechanism of Arylation of Ethylene by Palladium", Reaction Kinetics and Catalysis Letters, Vol. 5, No. 1, 61–65 (1976) discloses a process for phenylating ethylene with benzene in the presence of palladium acetate. Hong, P., and Yamazaki, H., "Rhodium Carbonyl-Catalyzed Activation of Carbon-Hydrogen Bonds for Application in Organic Synthesis. V. Phenylation of Olefins with Benzenes," Journal of Molecular Catalysis, Vol. 26, p. 297 (1984) discloses a process for the reaction of ethylene with benzene under carbon monoxide pressure in the presence of a rhodium carbonyl catalyst. Shimuzu, K. and Ohta, N., Chemical Abstracts AN #CA89(12):90442k (1978) discloses a process for producing styrenes in one step from the olefin and aromatic compound using heterogeneous rhodium or iridium catalysts on inorganic supports. In view of the foregoing, it would be desirable to produce a one-step process for the production of vinyl aromatic compounds which is more selective than the one-step processes of the prior art.

SUMMARY OF THE INVENTION

In one aspect, this invention is a process for the preparation of vinyl aromatic compounds which comprises contacting an aromatic compound and an olefin in the presence of a catalytic amount of a cyclopentadienyl, indenyl, or fluorenyl rhodium complex under reaction conditions sufficient to form the corresponding vinyl aromatic compound. Surprisingly, the catalysts used in the process of this invention provide higher selectivity than prior art catalysts used in one-step processes. Also, they are more stable than prior art catalysts used in one-step processes, which provides higher conversion rates in the vinylation process. In a second and third aspect, this invention is an alkyl- or trimethylsilyl-substituted indenyl rhodium complex or fluorenyl rhodium complex which is suitable for use in the above process for the vinylation of aromatic compounds.

DETAILED DESCRIPTION OF THE INVENTION

In its first aspect, this invention is a process for the preparation of vinyl aromatic compounds which comprises contacting an aromatic compound and an olefin in the presence of a catalytic amount of a cyclopentadienyl (Cp), indenyl (In), or fluorenyl rhodium complex under reaction conditions sufficient to form the corresponding vinyl aromatic compound.

The aromatic compound to be vinylated in this process may be any compound which contains an aromatic ring which is carbocyclic or heterocyclic. The aromatic ring is optionally substituted with moieties which do not interfere with the vinylation of the aromatic ring. Preferably, the aromatic compound is selected from the group comprising anisole, benzene, toluene, biphenyl, or ethyl benzene, and is more preferably anisole or benzene.

The olefin employed in this vinylation process is a $C_{1-20}$ unsaturated aliphatic hydrocarbon having one or more double bonds. Preferably, the olefin employed is a $C_{1-10}$ olefin, more preferably is ethylene, propylene, butene, or pentene and most preferably is ethylene.

The process of this invention uses catalysts which are either cyclopentadienyl (Cp), indenyl (In), or fluorenyl rhodium complexes. Preferably, the rhodium substituent has ligands selected from the group comprising $C_{1-20}$ alkene, carbonyl, phosphino, phosphito, arsino, stibino, and isonitrilo. The phosphino ligand may optionally be substituted with alkyl or aryl groups. "Phosphito" as used herein refers to a phosphino ligand which is substituted with alkoxy or aryloxy groups. The cyclopentadienyl, indenyl, or fluorenyl rings may either be substituted or unsubstituted. If substituted, the rings are preferably substituted with primary or secondary $C_{1-20}$ alkyl or alkylsilyl, halo, cyano, carboalkyl, carboaryl, carboaryloxy, carboalkoxy, alkylthio, or arylthio moieties. These catalysts may be supported on a suitable carrier material such as, for example, alumina, titania, zeolites, or diatomaceous earth.

Preferred cyclopentadienyl (Cp) rhodium complexes have the following structure:

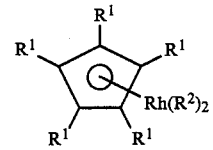

wherein each $R^1$ is separately a hydrogen, or a primary or secondary $C_{1-20}$ alkyl or alkylsilyl, halo, cyano, carboalkyl, carboaryl, carboaryloxy, carboalkoxy, alkylthio, or arylthio moiety and $R^2$ is separately in each occurrence a $C_{1-20}$ alkene, carbonyl, phosphino, phosphito, arsino, stibino, or isonitrilo moiety. Preferably, $R^2$ is a $C_{1-20}$ alkene, phosphito, arsino, stibino, or isonitrilo ligand, and more preferably is a $C_{1-20}$ alkene. Most preferably, $R^2$ is ethylene or propylene.

Preferred indenyl (In) rhodium complexes have the following structure:

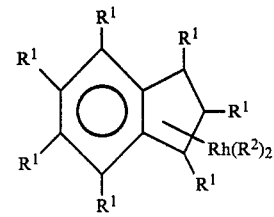

wherein each $R^1$ is separately a hydrogen, or a primary or secondary $C_{1-20}$ alkyl or alkylsilyl, halo, cyano, carboalkyl, carboaryl, carboaryloxy, carboalkoxy, alkylthio, or arylthio moiety and $R^2$ is separately in each occurrence a $C_{1-20}$ alkene, carbonyl, phosphino, phosphito, arsino, stibino, or isonitrilo moiety. Preferably, at least one $R^1$ is a $C_{2-20}$ alkyl or $C_{1-20}$ alkylsilyl moiety. Preferably, $R^2$ is a $C_{1-20}$ alkene, phosphito, arsino, stibino, or isonitrilo ligand, and more preferably is a $C_{1-20}$ alkene. Most preferably, $R^2$ is ethylene or propylene.

Preferred fluorenyl rhodium complexes have the following structure:

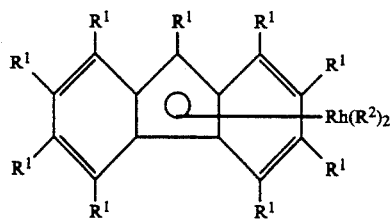

wherein each $R^1$ is separately a hydrogen, or a primary or secondary $C_{1-20}$ alkyl or alkylsilyl, halo, cyano, carboalkyl, carboaryl, carboaryloxy, carboalkoxy, alkylthio, or arylthio moiety, and $R^2$ is separately in each occurrence a $C_{1-20}$ alkene, carbonyl, phosphino, phosphito, arsino, stibino, or isonitrilo ligand. Preferably, $R^2$ is a $C_{1-20}$ alkene, phosphito, arsino, stibino, or isonitrilo ligand, and more preferably is a $C_{1-20}$ alkene. Most preferably, $R^2$ is ethylene or propylene.

These complexes may be prepared by contacting an alkali metal cyclopentadienide, indenide, or fluorenide with dimeric rhodium chlorobisethylene under reaction conditions sufficient to form the corresponding cyclopentadienyl, indenyl, or fluorenyl rhodium bisethylene complex. The rhodium bisethylene complex is then contacted with a $C_{1-20}$ alkene, phosphine, phosphite, arsine, stibine, or nitrile in a hydrocarbon medium under reaction conditions sufficient for the alkene, phosphine, phosphite, arsine, stibine, or nitrile to displace ethylene and form the corresponding rhodium complex. For example, indene rhodium bisethylene may be prepared by contacting chlorobis(ethylene)rhodium(I) dimer with lithium indenide. Similarly, 1,2,3-trimethylindene rhodium bisethylene may be prepared by contacting chlorobis(ethylene)rhodium(I) dimer with lithium 1,2,3-trimethylindenide.

The alkali metal cyclopentadienide, indenide, or fluorenide is prepared by contacting the corresponding cyclopentadienyl, indenyl, or fluorenyl compound with a solution of an alkali metal alkyl in a hydrocarbon or ether solvent, under reaction conditions sufficient to form the alkali metal cyclopentadienide, indenide, or fluorenide salt. Preferably, the alkali metal alkyl is butyl lithium. Hexane or pentane is the most preferred solvent, although ethyl ether or tetrahydrofuran may also be employed. When a solvent is employed, it is preferably present in an amount of from about 5 parts to about 40 parts, and more preferably in an amount of from about 10 parts to about 30 parts to one part of cyclopentadienyl, indenyl, or fluorenyl substrate. The reaction is preferably carried out at about 25° C. The reaction time will depend on the reactants employed, but is most preferably about two hours.

To prepare the cyclopentadienyl, indenyl, or fluorenyl rhodium complex, the alkali metal cyclopentadienide, indenide, or fluorenide salt is preferably contacted with the dimeric rhodium chlorobisethylene complex in an organic solvent. Preferably, the solvent is tetrahydrofuran (THF). The solvent is preferably present in an amount of from about 25 parts to about 125 parts, and more preferably in an amount of from about 25 parts to about 50 parts to one part of dimeric rhodium complex. The reactants are preferably contacted at a temperature in the range from about −50° C. to about 25° C., and more preferably at about −30° C. to form a reaction mixture. The reaction temperature of the reaction mixture is then brought to about 25° C. The reaction time will depend on the reactants employed, but is preferably between about 1 and 6 hours, and more preferably about 3 to 6 hours.

The process of the invention for the preparation of vinyl aromatic compounds may be carried out in any suitable reaction vessel. Preferred reaction temperatures depend on the reactivity of the particular aromatic compound employed and may range from about 25° C. to about 300° C. More preferably, the reaction temperature is above about 100° C., and most preferably above about 150° C. More preferably, the optimum reaction temperature is no greater than about 230° C. and most preferably no greater than about 210° C. The preferred temperature ranges optimize the reaction rate, prevent the catalyst of the invention from decomposing, and aid in preventing the formation of hydrogenated products.

Process reaction times depend on the reactivity of the reagents employed, the ratios of reactants, and the process temperature, and may range from about 1 minute to about 200 hours. Advantageously, the reaction time is sufficiently long to enable the control of the reaction rate and is preferably longer than about 1 hour. The reaction time is advantageously short enough to enable the commercial practice of the invention and is preferably shorter than about 10 hours.

Process reaction pressures depend on choice of reagents and the process temperature employed and preferably are above about 50 mm Hg, more preferably above about 100 psig, and most preferably above about 200 psig, and are preferably below about 5000 psig, more preferably below about 2000 psig, and most preferably below about 1000 psig. The process of the invention may be carried out neat or in solution. The weight ratio of solvent to aromatic substrate preferably ranges from about 0 to about 10 percent.

Preferred molar ratios of the aromatic compound:olefin range from at least about 0.1 to below about 10. More preferably, the molar ratio is at least about 0.5 and most preferably is at least about 0.75. More preferably, the molar ratio is no greater than about 5, and most preferably is no greater than about 1. A catalytic amount of the rhodium complex is required for the practice of this invention. The amount of rhodium catalyst employed is advantageously determined by the efficiency of a particular catalyst at a particular temperature, pressure, and solvent concentration, reactor capacity, and ease of purification of the reaction product. Preferably, the amount of catalyst employed relative to the amount of aromatic substrate ranges from at least about 0.001 weight percent, more preferably at least about 0.05 weight percent, and most preferably at least about 0.1 weight percent to no greater than about 50 weight percent, more preferably no greater than about 5 weight percent, and most preferably no greater than about 1 weight percent.

In a second aspect, this invention is a novel indenyl rhodium complex of the following formula:

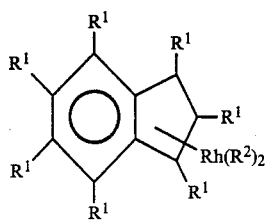

wherein each $R^1$ is separately a hydrogen, or a primary or secondary $C_{1-20}$ alkyl or alkylsilyl, halo, cyano, carboalkyl, carboaryl, carboaryloxy, carboalkoxy, alkylthio, or arylthio moiety and $R^2$ is separately in each occurrence a $C_{1-20}$ alkene, carbonyl, phosphino, phosphito, arsino, stibino, or isonitrilo moiety, wherein at least one $R^1$ is a $C_{1-20}$ alkyl or $C_{1-20}$ alkylsilyl moiety. Preferably, $R^2$ is a $C_{1-20}$ alkene, phosphito, arsino, stibino, or isonitrilo ligand, and more preferably is a $C_{1-20}$ alkene. Most preferably, $R^2$ is ethylene. This compound may be prepared by reacting indenyl salts and dimeric rhodium chlorobisethylene, as described above.

In a third aspect, this invention is a novel fluorenyl rhodium complex of the following formula:

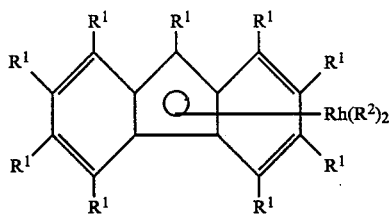

wherein each $R^1$ is separately a hydrogen, or a primary or secondary $C_{1-20}$ alkyl or alkylsilyl, halo, cyano, carboalkyl, carboaryl, carboaryloxy, carboalkoxy, alkylthio, or arylthio moiety and $R^2$ is separately in each occurrence a $C_{1-20}$ alkene, carbonyl, phosphino, phosphito, arsino, stibino, or isonitrilo moiety, wherein at least one $R^1$ is a $C_{1-20}$ alkyl or $C_{1-20}$ alkylsilyl moiety. Preferably, $R^2$ is a $C_{1-20}$ alkene, phosphito, arsino, stibino, or isonitrilo ligand, and more preferably is a $C_{1-20}$ alkenyl. Most preferably, $R^2$ is ethylene. This compound may be prepared by reacting fluorenyl salts and dimeric rhodium chlorobisethylene, as described above.

ILLUSTRATIVE EMBODIMENTS

The following examples are given to illustrate the invention and should not be interpreted as limiting it in any way. Unless stated otherwise, all parts and percentages are given by weight.

Reactions are run in glass liners (147 mm long, 41 mm I.D., 45 mm O.D.) which are wrapped with a few turns of teflon tape near the top to provide a tight fit to minimize spillover of contents from the glass liner into the reaction vessel, a 300-cc Autoclave Engineers, Inc. Magnedrive Packless Autoclave. An external heater and internal cooling coils are used to maintain the reaction temperature. The reactor is cleaned between runs in concentrated $HNO_3$. Reaction mixtures are analyzed on a Hewlett-Packard (HP) 5710A (FID) gas chromatograph connected to a HP 3390A reporting integrator or a Spectra Physics 4270 reporting integrator interfaced to an IBM PC-AT through Spectra Physics LAB-NET software. A 25 m HP fused silica capillary column coated with high temperature 5 percent phenylmethylsilicone (0.33 μm film, 0.2 mm I.D.) is used with a carrier gas (He) flow rate of 1 ml/min at 15 psig and 100/1 split ratio. Injection port and detector temperatures are 250° C. and 300° C., respectively. $^1H$ and $^{13}C$ NMR spectra are obtained on a JEOL FX-90Q Spectrometer equipped with a broadband, tunable probe operating at 36.2 MHz. GLC-mass spectra are obtained on a HP model 5985B equipped with a capillary column similar to the one described above. Unless otherwise specified, all chemicals are reagent grade and used as received. Liquids were degassed and dried by standard techniques prior to use. Ethylene and propylene were research purity from Matheson Chemical Co.

EXAMPLE 1

Ethylenation of Anisole Catalyzed by $(CH_3)_5CpRh(C_2H_4)_2$

A sealed autoclave containing a glass liner that has been oven dried is purged with argon. A 10-ml anisole solution of 147 mg (0.5 mmole) of the Rh catalyst is introduced by syringe through a dip tube capped with a rubber septum. Another 50 ml of anisole is added the same way to wash the syringe into the reaction vessel. After purging with argon again to remove traces of air, the reactor is pressurized with ethylene to 400 psig at 25° C. The first sample, a clear yellow solution characteristic of the catalyst, is withdrawn through the dip tube before turning on the heater. The temperature is brought up to 150° C. and held there for 28 hours. GLC analysis of samples taken periodically reveals only a trace of vinyl product, so the temperature is increased to 180° C. and held there for an additional 48 hours. Samples are still clear yellow solutions and quantitative analysis using decane as the internal standard reveals a steady conversion to m-vinylanisole. The temperature is increased again to 210° C. and held for 25 hours. The reaction rate increases sharply at first, but as the samples get progressively darker, the reaction rate decreases and stops for a final yield of 798 mg (5.96 mmoles), corresponding to 11.9 mmoles of product per mmole of Rh initially charged, after 5 hours at that temperature. In addition, GLC-mass spectral analysis reveals the conversion of some of the m-vinylanisole to a mixture of isomers of divinylanisole and to ethylanisole and ethylvinylanisole, products of Rh metal catalyzed hydrogenation. The reactor is cooled and 41 ml of dark brown reaction mixture is recovered. Distillation at reduced pressure (0.5 mm Hg) yields a small amount of colorless liquid at 40° C. The $^1H$ and $^{13}C$ NMR spectra taken in $CD_2Cl_2$ are characteristic of m-vinylanisole. After 7.3 turnovers, the selectivity to m-vinylanisole is 99 percent.

EXAMPLE 2

Ethylenation of Anisole Catalyzed by $(CH_3)_5CpRh(CO)_2$

The sealed autoclave containing a glass liner that has been oven dried is purged with argon. A 10-ml anisole solution of 147 mg (0.5 mmole) of the Rh catalyst is introduced by syringe through a dip tube capped with a rubber septum. Another 50 ml of anisole is added the same way. After purging with argon again, the reactor is pressurized with ethylene to 500 psig at room temperature. The first sample, a clear red solution characteristic of the catalyst, is withdrawn through the dip tube before turning on the heater. The temperature is raised over a one-hour period to 175° C. (at 680 psig) and the color of the reaction mixture turns yellow, characteristic of (CH$_3$)$_5$CpRh(C$_2$H$_4$)$_2$. GLC-mass spectral analysis also reveals the conversion of most of the dicarbonyl Rh complex to the bisethylene complex. The temperature is raised again to 180° C. and held there for an additional 16 hours. The reaction mixture darkens and GLC analysis reveals a trace of vinylanisole. The temperature is raised to 200° C.–210° C. for an additional day and the reaction mixture progressively blackens while the production of m-vinylanisole first increases rapidly then levels off as in the reaction described in Example 1. Quantitative GLC analysis using decane as the internal standard shows a maximum yield of m-vinylanisole of 195 mg (1.46 mmoles) corresponding to 2.9 mmoles of product per mmole of Rh initially charged. GLC analysis also reveals the conversion of some of the m-vinylanisole to divinylanisole and m-ethylanisole, a product of Rh metal catalyzed hydrogenation. After 2.75 turnovers, the selectivity to m-vinylanisole is 95 percent.

EXAMPLE 3

Propenylation of Anisole Catalyzed by (CH$_3$)$_5$CpRh(CO)$_2$

In this experiment propylene is charged into a reactor containing an ethylenation reaction mixture that has been allowed to run long enough to demonstrate catalytic activity similar to what is observed in the ethylenation reaction catalyzed by (CH$_3$)$_5$CpRh(CO)$_2$ This procedure is followed because it is feared that propylene might be so much less reactive than ethylene that even small inhibiting influences might interfere with the detection of propenylanisole. Thus, an ethylenation reaction is set up as follows: the sealed autoclave containing a glass liner that has been oven dried is purged with argon. A 10-ml anisole solution of 147 mg (0.5 mmole) of the Rh catalyst is introduced by syringe through a dip tube capped with a rubber septum. Another 50 ml of anisole is added the same way. After purging with argon again, the reactor is pressurized with ethylene to 500 psig at room temperature. The temperature is raised to 180° C. (at 680 psig) and, over a four-hour period, both GLC-mass spectral analysis and the change of color from red to yellow reveal the conversion of the initially charged dicarbonyl rhodium complex to (CH3)5CpRh(C2H4)2. After an additional 16 hours at 175° C., a small amount of m-vinylanisole is detected. An additional 2 hours at 190° C. results in considerably more rapid production of m-vinylanisole. At this point the reactor is cooled then vented then charged with propylene. After 1.5 turnovers, the selectivity to m-vinylanisole is 85 percent. Samples from this point on are deep blue in color. The temperature is raised to 200° C. (at 330 psig) over a two-hour period and held there for an additional 2 hours. GLC-mass spectral analysis indicates the production of small amounts of propenylanisole. The temperature is raised again to 210° C. and held there 21 hours then to 220° C. for an additional 16 hours. During this time GLC and GLC-mass spectral analysis indicate the production of about 100 mg of a mixture of two isomers of propenylanisole.

EXAMPLE 4

Preparation of Indene Rhodium Bisethylene, InRh(C$_2$H$_4$)$_2$

All operations were performed under an inert atmosphere and with dry, degassed solvents. A cooled solution (−30° C.) of 672 mg (5.48 mmoles) of lithium indenide in 40 ml of THF is added in a slow stream to a cooled slurry of 1.0 g (2.54 mmoles) of chlorobis(ethylene)rhodium(I)dimer in THF. The rust-colored slurry is stirred 30 minutes at room temperature after the addition is complete, then stripped of solvent at reduced pressure The black residue is taken up in hexane and passed through a 6-inch column of activated neutral alumina wit hexane eluent. A yellow fraction is collected and 1.16 g of yellow crystals are recovered (83 percent). The $^1$H and $^{13}$C NMR spectra agreed with published spectra.

EXAMPLE 5

Ethylenation of Toluene Catalyzed by InRh(C$_2$H$_4$)$_2$

The sealed autoclave containing a glass liner that has been oven dried is purged with argon. A 10-ml toluene solution of 140 mg (0.51 mmole) of the Rh catalyst is introduced by syringe through a dip tube capped with a rubber septum. Another 50 ml of toluene are added the same way. After purging with argon again, the reactor is pressurized with ethylene to 700 psig at room temperature. The first sample is withdrawn before turning on the heater. The temperature is increased to 170° C. (the pressure rises to 1800 psig) and held there for 20 hours without a sign of reaction. After 2 hours at 205° C., the reaction mixture darkens slightly and analysis by GLC-mass spectrometry reveals an increase in indene (indicative of catalyst decomposition) and a trace of vinyltoluene. Continued heating at about 200° C. for 7 more hours only results in a darker color and minor increases in indene and vinyltoluene. An additional 48 hours at about 200° C. results in no further increase in indene or vinyltoluene.

EXAMPLE 6

Ethylenation of Anisole Catalyzed by InRh(C$_2$H$_4$)2

The sealed autoclave containing a glass liner that has been oven dried is purged with argon. A 10-ml anisole solution of 140 mg (0.51 mmole) of the Rh catalyst is introduced by syringe through a dip tube capped with a rubber septum. Another 50 ml of anisole is added the same way. After purging with argon again, the reactor is pressurized with ethylene to 700 psig at room temperature. The first sample is withdrawn before turning on the heater. The temperature is increased to 135° C. in one hour then to 150° C. in the next 2 hours, but there is no sign of reaction until the temperature reaches 160° C. and the pressure is about 900 psig. Vinylanisole, determined by comparison of the GLC-mass spectrum with that of authentic m-vinylanisole, is produced slowly over a period of 2 days under the latter conditions. GLC and GLC-mass spectral analysis also reveal a slow increase in the production of indene, indicative of catalyst decomposition. Quantitative GLC analysis using octadecane as the internal standard reveals the production of about 12 mg (0.09 mmole) of a mixture of meta and para vinylanisole in a 13/1 ratio, respectively, which corresponds to 0.2 mmole of product per mmole of Rh initially charged. After 0.2 turnovers, the selectivity to vinylanisole is at least 90 percent.

EXAMPLE 7

Ethylenation of Toluene Catalyzed by In(TMS)$_2$Rh(C$_2$H$_4$)$_2$

Using the same setup as in Example 1, a 10-ml toluene solution of 210 mg (0.5 mmole) of the indenyl trimethylsilyl (TMS) rhodium bisethylene catalyst is introduced by syringe through a dip tube capped with a rubber septum. Another 50 ml of toluene is added the same way. After purging with argon again, the reactor is pressurized with ethylene to 700 psig at 25° C. The first sample, a clear yellow solution, is withdrawn through the dip tube before turning on the reactor temperature controls. The reaction temperature is increased to 100° C. and held there for 18 hours without a sign of reaction. Reaction commences at about 175° C., where the temperature is held for 22 hours. The production of vinyltoluene at this temperature is slow, and the temperature is increased to 185° C.–205° C. At this temperature, however, reaction samples darken and GLC analysis shows a loss of bisTMSindene, a buildup of indene, and the stoppage of vinyltoluene production, indicating catalyst decomposition. Only the meta and para isomers of vinyltoluene are produced in a 2.5 to 1 ratio. Quantitative GLC analysis using 4-ethyltoluene as an internal standard reveals a 134-mg (1.1 mmoles) yield of vinyltoluene, representing 2.2 turnovers based on the 0.5 mmole of catalyst initially charged, with a selectivity of at least 95 percent.

EXAMPLE 8

Ethylenation of Anisole Catalyzed by In(TMS)$_2$Rh(C$_2$H$_4$)$_2$

The sealed autoclave containing a glass liner that has been oven dried is purged with argon. A 10-ml anisole solution of 210 mg (0.5 mmole) of the Rh catalyst is introduced by syringe through a dip tube capped with a rubber septum. Another 50 ml of anisole is added the same way. After purging with argon again, the reactor is charged with ethylene at room temperature. The first sample is withdrawn before turning on the heater. The temperature is increased to 150° C. (at 640 psig of ethylene) in one hour and held there for 5 days while vinylanisole, determined by comparison of the GLC-mass spectrum with that of authentic m-vinylanisole, is produced slowly. The reaction mixture turns dark brown and GLC analysis shows traces of indene. The temperature is increased to 190° C. and the production of vinylanisole and indene accelerates and the reaction mixture blackens. Quantitative GLC analysis using octadecane as the internal standard reveals the production of about 76 mg (0.83 mmole) of a mixture of meta and para vinylanisole in a 11/1 ratio, respectively, corresponding to 1 mmole of product per mmole of Rh initially charged. The selectivity of vinylanisole is at least 95 percent.

EXAMPLE 9

Ethylenation of Ethylbenzene Catalyzed by In(TMS)$_2$Rh(C$_2$H$_4$)$_2$

The sealed autoclave containing a glass liner that has been oven dried is purged with argon. A 10-ml ethylbenzene solution of 210 mg (0.5 mmole) of the Rh catalyst is introduced by syringe through a dip tube capped with a rubber septum. Another 50 ml of ethylbenzene is added the same way. After purging with argon again, the reactor is charged with ethylene at room temperature The first sample is withdrawn before turning on the heater. The temperature is increased to 170° C. (at 670 psig of ethylene). After 4 hours a trace of ethylstyrene, determined by GLC-mass spectral analysis, appears. The temperature is increased to 178° C.–185° C. (at 700 psig) and ethylstyrene is produced slowly over an 18-hour period. Quantitative GLC analysis using octadecane as the internal standard reveals the product of about 22 mg (0.17 mmole) of a mixture of two isomers of ethylstyrene in a 2.5/1 ratio corresponding to 0.3 mmole of product per mmole of Rh initially charged. GLC-mass spectral analysis also indicates the presence of diethylbenzene, the product of hydrogenation of ethylstyrene. In addition GLC and GLC-mass spectral analysis reveal the presence of indene, the product of catalyst decomposition. Trimethylsilylindene is also detected by GLC-mass spectral analysis. Finally, the temperature is increased to 200° C. for 5 hours resulting in only a minor increase in ethylstyrene; however, the formation of diethylbenzene and indene increases significantly to about 0.17 mmole of each. The selectivity to ethylstyrene is at least 80 percent.

EXAMPLE 10

Ethylenation of para-Xylene Catalyzed by In(TMS)$_2$Rh(C$_2$H$_4$)$_2$

The sealed autoclave containing a glass liner that has been oven dried is purged with argon. A 10-ml p-xylene solution of 210 mg (0.5 mmole) of the Rh catalyst is introduced by syringe through a dip tube capped with a rubber septum. Another 50 ml of p-xylene is added the same way. After purging with argon again, the reactor is charged with ethylene at room temperature. The first sample, light orange in color characteristic of the catalyst, is withdrawn before turning on the heater. The temperature is increased over a three-hour period to 175° C. (at 700 psig of ethylene). Despite holding the temperature at 180° C. for 2 days, no vinylation product, vinylxylene, is detected; however, the samples progressively lose their color and indene, determined by comparison of the GLC-mass spectrum with that of authentic indene, is produced. Increasing the temperature to 210° C. for 3–4 hours only results in more indene.

EXAMPLE 11

Ethylenation of Biphenyl Catalyzed by In(TMS)$_2$Rh(C$_2$H$_4$)$_2$

The sealed autoclave containing a glass liner that has been oven dried is purged with argon. Biphenyl (13 g, 84 mmoles) in 50 ml of p-xylene is charged into the autoclave and a 10-ml p-xylene solution of 210 mg (0.5 mmole) of the Rh catalyst is introduced by syringe through a dip tube capped with a rubber septum. After purging with argon again, the reactor is charged with ethylene at room temperature. The first sample, light orange color characteristic of the catalyst, is withdrawn before turning on the heater. The temperature is increased over a two-hour period to 180° C. (at 450 psig of ethylene). The reactor is held at 160° C. for an additional 10 hours then at 185° C. for 7 hours more. p-Vinylbiphenyl and another isomer of vinylbiphenyl, determined by comparison of the GLC-mass spectrum with that of authentic p-vinylbiphenyl, are slowly produced in a ratio of 1/2, respectively. In this case also, GLC analysis shows that vinylation is accompanied by a slow increase in the amount of indene, suggestive of decomposition of the indenyl rhodium complex.

EXAMPLE 12

Ethylenation of Anisole Catalyzed by In(i-Pr)Rh($C_2H_4$)$_2$

The sealed autoclave containing a glass filler that has been oven dried is purged with argon. A 10-ml anisole solution of 150 mg (0.5 mmole) of the isopropyl indene rhodium bisethylene catalyst is introduced by syringe through a dip tube capped with a rubber septum. Another 50 ml of anisole is added the same way. After purging with argon again, the reactor is charged with ethylene at room temperature. The temperature is increased to 195° C. (at 730 psig of ethylene) over a period of 3 hours at which point vinylanisole is first detected by GLC analysis. After another hour under these conditions, the reaction mixture darkens. The temperature is increased slightly to 200° C. and held there 3 days, during which time increasing amounts of vinylanisole, determined by comparison of the GLC-mass spectrum with that of authentic m-vinylanisole, are produced. Quantitative GLC analysis using decane as the internal standard reveals the production of about 117 mg (0.88 mmole) of a mixture of meta and para vinylanisole in a 29/1 ratio, respectively, corresponding to 1.76 mmoles of product per mmole of Rh initially charged. The selectivity to vinylanisole is at least 95 percent.

COMPARATIVE EXAMPLE 1

Ethylenation of Toluene at Low Pressure Catalyzed by In(TMS)$_2$Rh($C_2H_4$)$_2$ The sealed autoclave containing a glass liner that has been oven dried is purged with argon. A 10-ml toluene solution of 210 mg (0.5 mmole) of the Rh catalyst is introduced by syringe through a dip tube capped with a rubber septum. Another 50 ml of toluene is added the same way. After purging with argon again, the reactor is pressurized with ethylene to 40 psig at room temperature. The first sample is taken before turning the heater on. The temperature is increased to 140° C. over a four-hour period at which point the reaction mixture blackens and GLC analysis shows only bisTMSindene from the catalyst. The reaction mixture is held at 140° C. and 20 psig for 5 days and GLC analysis shows complete conversion of the bisTMSindene to indene, indicative of catalyst decomposition, but no vinyltoluene.

EXAMPLE 13

Preparation of 1,2,3-Trimethylindene Rhodium Bisethylene, 1,2,3-(CH$_3$)$_3$InRh(C$_2$H$_4$)$_2$ All operations are performed under an inert atmosphere and with dry, degassed solvents. A cooled solution (−30° C.) of 180 mg (1.1 mmoles) of lithium 1,2,3-trimethylindenide in 5 ml of THF is added in a slow stream to a cooled slurry of 194 mg (0.5 mmole) of chlorobis(ethylene)rhodium(I)dimer in 5 ml of THF. The mixture darkens as it comes to room temperature. The mixture is stirred an additional hour at room temperature then the solvent is stripped off under reduced pressure. The black residue is taken up in hexane and passed through a 6-inch column of activated neutral alumina with hexane eluent. A bright yellow fraction yields 230 mg of a crude yellow solid after removal of hexane (73 percent yield). Recrystallization from pentane yields yellow needles with a melting point of 118° C. and a decomposition point of 150° C. The $^1$H and $^{13}$C NMR spectra are consistent with the proposed structure and similar to those for the known complexes, InRh(C$_2$H$_4$)$_2$ and 1-MethylInRh(C$_2$H$_4$)$_2$.

EXAMPLE 14

Preparation of Lithium 1-(Trimethylsilyl)indenide, 1-[Si(CH$_3$)$_3$]InLi

All operations were performed under an inert atmosphere and with dry, degassed solvents. A solution of 0.83 ml (1.33 mmoles) of 1.6 M butyl lithium in hexane is added dropwise, rapidly from a syringe to a stirred solution of 280 mg (1.33 mmoles) of 1-trimethylsilylindene in hexane at room temperature. A white precipitate appeared after 2 hours at room temperature. The white suspension is filtered and washed with hexane after having stood overnight at room temperature. The dried lithium salt is recovered in 77 percent yield (200 mg: 1.03 mmoles).

EXAMPLE 15

Preparation of 1-Trimethylsilylindene Rhodium Bisethylene, 1-Si(CH$_3$)$_3$InRh(C$_2$H$_4$)$_2$ All operations are performed under an inert atmosphere and with dry, degassed solvents. A cooled solution (−30° C.) of 200 mg (1.03 mmoles) of lithium 1-trimethylsilylindenide in 5 ml of THF is added in a slow stream to a cooled slurry of 190 mg (0.49 mmole) of chlorobis(ethylene)rhodium(I)dimer in 5 ml of THF. The mixture darkens as it comes to room temperature. The mixture is stirred an additional 3-6 hours at room temperature then filtered and the solvent is stripped off under reduced pressure. The black residue is taken up in hexane and passed through a 6-inch column of activated neutral alumina with hexane eluent. A bright yellow fraction yields 340 mg of a yellow-orange oil (97 percent yield) which crystallizes to yellow platelets (melting point 60° C.-62.5° C.: decomposition point 150° C.-170° C.). The $^1$H and $^{13}$C NMR spectra are consistent with the proposed structure and similar to those for the known complexes, InRh(C$_2$H$_4$)$_2$ and 1-MethylInRh(C$_2$H$_4$)$_2$.

EXAMPLE 16

Preparation of Lithium 1,3-Bis(trimethylsilyl)indenide, 1,3-[Si(CH$_3$)$_3$]$_2$InLi All operations are performed under an inert atmosphere and with dry, degassed solvents. A solution of 2.50 ml (4.0 mmoles) of 1.6 M butyl lithium in hexane is added rapidly from a syringe to a stirred solution of 1 04 g (4.0 mmoles) of a one to one mixture of 1,1- and 1,3-bis(trimethylsilyl)indene in hexane at room temperature. A white precipitate appeared after 2 hours at room temperature. After having stood a few days at room temperature, filtration yielded 470 mg (1.76 mmoles). The filtrate, after standing another 3 weeks at room temperature yielded another 180 mg of lithium salt. Allowing the filtrate to stand an additional 5 weeks at room temperature yielded 100 mg more for a total of 750 mg (75 percent yield). Apparently, 1,3-bis(trimethylsilyl)indene is converted to the lithium salt within a few days but 1,1-bis(trimethylsilyl)indene does not react with butyl lithium; it must first isomerize to the 1,3-isomer which then can be converted to the lithium salt.

EXAMPLE 17

Preparation of 1,3-Bistrimethylsilylindene Rhodium Bisethylene, 1,3-[Si(CH$_3$)$_2$]$_2$InRh(C$_2$H$_4$)$_2$ All operations are performed under an inert atmosphere and with dry, degassed solvents. A cooled solution (−30° C.) of 420 mg (1.58 mmoles) of lithium 1,3-bis(trimethylsilyl)indenide in 10 ml of THF is added in a slow stream to a cooled THF slurry of 280 mg (0.72 mmole) of chlorobis(ethylene)rhodium(I)dimer in 10 ml of THF. The mixture darkens as it comes to room temperature. The mixture is stirred an additional 3-6 hours at room temperature then filtered and the solvent is stripped off. The black residue is taken up in hexane and passed through a 6-inch column of activated neutral alumina with hexane eluent. An orange-red band which passes through rapidly is collected in two fractions, the first of which yields 450 mg and the second yields 30 mg for a total yield of 480 mg of a deep red-orange solid (80 percent yield) with a melting point of about 99° C. The $^1$H and $^{13}$C NMR spectra are consistent with the proposed structure and similar to those for the known complexes, InRh(C$_2$H$_4$)$_2$ and 1-MethylInRh(C$_2$H$_4$)$_2$.

EXAMPLE 18

Preparation of 1-Isopropylindene and Bisisopropylindene

All operations are performed under an inert atmosphere and with dry, degassed solvents. A solution of 180 ml (0.29 mmole) of 1.6 M butyl lithium in hexane is added dropwise to a stirred solution of 29.0 g (0.25 mmole) of indene (Aldrich, gold label) in 200 ml of ether at room temperature. The ether solution is then added dropwise to an ether solution of 2-bromopropane. There is a mild exotherm and a precipitate of LiBr. The reaction mixture is stirred overnight at room temperature then filtered. The filtrate is concentrated under reduced pressure then washed with several portions of water. The ether layer is dried over sodium sulfate then solvent is stripped off under reduced pressure to an amber colored oil. GLC and GLC-mass spectral analysis of the oil revealed a mixture of isopropylindene (89 area percent), bisisopropylindene (7 area percent) and indene (4 area percent). The oil is distilled and a 20-g fraction, 96 percent pure by GLC area percent, is collected at 39° C. and 0.3 mm. Mass spectral and 1H and $^{13}$C NMR analyses are consistent with 1-isopropylindene. Another distillate fraction (approx. 2 g) collected at 62° C.-64° C. and 0.2 mm proves to be bisisopropylindene, according to mass spectral and $^{13}$C NMR analysis.

EXAMPLE 19

Preparation of Lithium 1-Isopropylindenide

All operations are performed under an inert atmosphere and with dry, degassed solvents. A solution of 20.0 ml (32.0 mmoles) of 1.6 M butyl lithium in hexane is added to a stirred solution of 5.06 g (32.0 mmoles) of 1-isopropylindene in 100 ml of hexane at room temperature. A white precipitate appeared after 30 minutes at room temperature. Filtration after 2 days at room temperature produces 2.8 g of white solid product. The filtrate is concentrated to 20 ml and, after standing at room temperature another week, an additional 1.9 g of product is recovered for a total of 4.7 g (89 percent yield).

EXAMPLE 20

Preparation of 1-Isopropylindene Rhodium Bisethylene, 1-CH(CH$_3$)$_2$InRh(C$_2$H$_4$)$_2$ All operations are performed under an inert atmosphere and with dry, degassed solvents. A cooled solution (−30° C.) of 520 mg (3.16 mmoles) of lithium 1-isopropylindenide in 20 ml of THF is added in a slow stream to a cooled slurry of 520 mg (1.34 mmoles) of chlorobis(ethylene)rhodium(I)dimer in 20 ml of THF. The mixture darkens as it comes to room temperature. The mixture is stirred an additional 6 hours at room temperature then the solvent is stripped off at reduced pressure. The black residue is taken up in hexane, filtered and passed through an 8-inch column of activated neutral alumina with hexane eluent. The yellow fraction is collected which yields 660 mg of a yellow oil (78 percent yield). The $^1$H and $^{13}$C NMR spectra confirm the formation of 1-isopropylindene rhodium bisethylene, 1-CH(CH$_3$)$_2$]InRh(C$_2$H$_4$)$_2$.

EXAMPLE 21

Preparation of 1,3-Bisisopropylindenide

All operations are performed under an inert atmosphere and with dry, degassed solvents. A solution of 5.0 ml (8.0 mmoles) of 1.6 M butyl lithium in hexane is added to a stirred solution of 1.5 g (7.5 mmoles) of bisisopropylindene in 30 ml of pentane at room temperature. A white precipitate appears in minutes at room temperature. Filtration after 2 days at room temperature produces 0.36 g of white solid product. The filtrate is concentrated and, after standing at room temperature another 4 days, an additional 0.18 g of product is recovered for a total of 0.54 g (36 percent yield) of 1,3-bisisopropylindenide.

EXAMPLE 22

Preparation of 1,3-Bisisopropylindene Rhodium Bisethylene, 1,3-[CH(CH$_3$)$_2$]$_2$InRh(C$_2$H$_4$)$_2$ All operations are performed under an inert atmosphere and with dry, degassed solvents. A cooled solution (−30° C.) of 500 mg (2.4 mmoles) of lithium 1,3-bisisoproylindenide in 20 ml of THF is added in a slow stream to a cooled slurry of 428 mg (1.1 mmoles) of chlorobis(ethylene)rhodium(1)dimer in 20 ml of THF. The mixture blackens even before the addition is complete. The mixture is stirred several hours at room temperature then the solvent is stripped off at reduced pressure. The black residue is taken up in hexane, filtered and passed through an 8-inch column of activated alumina with hexane eluent. The yellow fraction is collected which yields 710 mg of a yellow solid (83 percent yield). The $^1$H and $^{13}$C NMR spectra confirm the formation of 1,3-bisisopropylindene rhodium bisethylene.

EXAMPLE 23

Preparation of Lithium Pentamethylcyclopentadienide, (CH$_3$)$_5$CpLi

All operations are performed under an inert atmosphere with dry, degassed solvents. A solution of 2.9 ml (36.7 mmoles) of 1.6 M butyl lithium in hexane is added from a syringe to a stirred solution of 5.0 g (36.7 mmoles) of pentamethylcyclopentadiene in 25 ml of hexane at room temperature over a period of 15 minutes. The white suspension is stirred at room temperature an additional 2 hours, then it is filtered and washed several times with hexane. The dried lithium salt is recovered in 88 percent yield (4.6 g).

EXAMPLE 24

Preparation of Pentamethylcyclopentadiene Rhodium Bisethylene, $(CH_3)_5CpRh(C_2H_4)_2$ All operations are performed under an inert atmosphere and with dry, degassed solvents. Lithium pentamethylcyclopentaindenide powder (720 mg, 5.06 mmoles) is added in several portions to a cooled slurry of 1.0 g (2.54 mmoles) of chlorobis(ethylene)rhodium(I) dimer in 40 ml of THF. The mixture darkens as it comes to room temperature. The mixture is stirred several hours at room temperature then the solvent is stripped off at reduced pressure. The black residue is taken up in hexane, filtered and passed through a 6-inch column of activated neutral alumina with hexane eluent. The yellow fraction is collected which yields 980 mg of pentamethylcyclopentadiene rhodium bisethylene as a yellow solid (64 percent yield).

EXAMPLE 25

Ethylenation of Anisole Catalyzed by $In(i-Pr)_2Rh(C_2H_4)_2$

The sealed autoclave containing a glass liner that has been oven dried is purged with argon. A 10-ml anisole solution of 179 mg (0.5 mmole) of the diisopropyl indene rhodium bisethylene catalyst is introduced by syringe through a dip tube capped with a rubber septum. Another 50 ml of anisole is added the same way. After purging with argon again, the reactor is charged with ethylene at room temperature. The temperature is increased to 175° C.-180° C. (at 650 psig of ethylene) over a period of two hours at which point vinylanisole, determined by comparison of the GLC-mass spectrum with that of authentic m-vinylanisole, is first detected by GLC analysis. The temperature is increased slightly to 185° C.-190° C. and held there 3 days, during which time increasing amounts of vinylanisole are produced. GLC analysis reveals the production of m-vinylanisole and only traces of p-vinylanisole at a selectivity of at least 95 percent.

What is claimed is:

1. A process for the preparation of vinyl aromatic compounds which comprises contacting an aromatic compound and an olefin in the presence of a catalytic amount of a cyclopentadienyl rhodium complex of the following formula:

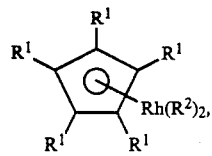

an indenyl rhodium complex of the following formula:

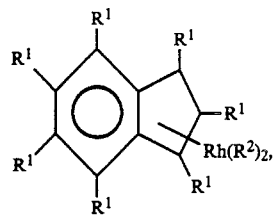

or a fluorenyl rhodium complex of the following formula:

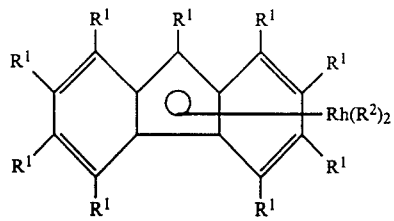

wherein each $R^1$ is separately a hydrogen, or a primary or secondary $C_{1-20}$ alkyl or alkylsilyl, halo, cyano, carboalkyl, carboaryl, carboaryloxy, carboalkoxy, alkylthio, or arylthio moiety and $R^2$ is separately in each occurrence a $C_{1-20}$ alkene, carbonyl phosphino, phosphito, arsino, stibino, or isonitrilo moiety; under reaction conditions sufficient to form the corresponding vinyl aromatic compound.

2. The process of claim 1 wherein the catalyst complex is a cyclopentadienyl rhodium complex.
3. The process of claim 2 wherein $R^2$ is a $C_{1-20}$ alkene.
4. The process of claim 3 wherein $R^2$ is ethylene.
5. The process of claim 3 wherein $R^2$ is propylene.
6. The process of claim 1 wherein the rhodium complex is an indenyl rhodium complex.
7. The process of claim 6 wherein $R^2$ is a $C_{1-20}$ alkene.
8. The process of claim 7 wherein $R^2$ is ethylene.
9. The process of claim 7 wherein $R^2$ is propylene.
10. The process of claim 1 wherein the rhodium complex is a fluorenyl rhodium complex.
11. The process of claim 10 wherein $R^2$ is a $C_{1-20}$ alkene.
12. The process of claim 10 wherein $R^2$ is ethylene.
13. The process of claim 10 wherein $R^2$ is propylene.

* * * * *